United States Patent [19]

Perine et al.

[11] Patent Number: 5,075,498

[45] Date of Patent: Dec. 24, 1991

[54] PROCESS FOR PREPARING SOLID BETAINES

[75] Inventors: Jeffrey W. Perine; Kim R. Smith; Joe D. Sauer; James E. Borland, all of Baton Rouge, La.

[73] Assignee: Ethyl Corporation, Richmond, Va.

[21] Appl. No.: 652,617

[22] Filed: Feb. 8, 1991

[51] Int. Cl.$^5$ .......................................... C07C 229/00
[52] U.S. Cl. .................................... 562/575; 562/553; 562/567
[58] Field of Search ........................ 562/575, 567, 553

[56] References Cited

U.S. PATENT DOCUMENTS

| | | | |
|---|---|---|---|
| 2,082,275 | 6/1937 | Daimler | 562/575 |
| 2,129,264 | 9/1938 | Downing | 562/575 |
| 2,564,507 | 8/1951 | Schaeffer | 562/575 |
| 2,800,502 | 7/1957 | Vassel | 562/575 |
| 3,480,665 | 11/1969 | Nagy | 562/575 |
| 3,555,079 | 1/1971 | Murumo | 260/501.13 |
| 3,649,677 | 3/1972 | Morris | 562/567 |
| 3,954,845 | 5/1976 | Martinsson | 562/567 |
| 4,832,871 | 5/1989 | Bade | 252/546 |

FOREIGN PATENT DOCUMENTS

1185111  3/1970  United Kingdom .

OTHER PUBLICATIONS

Nandakumar, "Journal of the Oil Technologists' Association of India," vol. 11 (2), pp. 31–34 (1979).

*Primary Examiner*—Michael L. Shippen
*Attorney, Agent, or Firm*—Patricia J. Hogan

[57] ABSTRACT

Betaines are produced in solid form by reacting a tert-amine with a haloalkanoate salt when the reaction is conducted in a polar aprotic solvent in which the betaine is substantially insoluble. In a preferred embodiment, the tert-amine is an N-alkyldimethylamine, the haloalkanoate is sodium chloroacetate, and the solvent is ethyl acetate.

20 Claims, No Drawings

PROCESS FOR PREPARING SOLID BETAINES

FIELD OF THE INVENTION

This invention relates to a process for preparing solid betaines by reacting a tert-amine with a haloalkanoate salt.

BACKGROUND

As disclosed in British Patent 1,185,111 (Morris) and U.S. Pat. Nos. 2,082,275 (Daimler et al.), 3,555,079 (Marumo et al.), and 4,832,871 (Bade), it is known that tert-amines can be quaternized with haloalkanoate salts in water or a polar protic organic solvent to prepare betaines in solution form, most commonly as 30-35% active aqueous solutions.

Solid betaines have the advantages over betaine solutions that they can be transported at lower costs and offer more flexibility in the formation of products from the betaines. It is possible to recover solid betaines from these solutions, but it would be preferable to be able to prepare the betaines directly in solid form.

SUMMARY OF INVENTION

It has now been found that betaines can be produced in solid form by the reaction of a tert-amine with a haloalkanoate salt when the reaction is conducted in a polar aprotic solvent in which the betaine is substantially insoluble.

DETAILED DESCRIPTION

As evidenced by the variety of types of tert-amines which have been quaternized with haloalkanoates in the past, the particular tert-amine used in the process is not critical. It may be, e.g., any of the tert-amines of Morris, Daimler et al., Marumo et al., and Bade, the teachings of all of which are incorporated herein by reference.

The tert-amines which are generally most valuable to employ in the reaction are those in which at least one of the N-substituents is an alkyl or hydroxyalkyl group and the remaining N-substituents are aliphatic or cyclic organic groups which may be hydrocarbyl or non-hydrocarbyl in nature, e.g., alkyl, hydroxyalkyl, polyoxyethylene, alkylamidoalkyl, phenyl, or benzyl, including those in which an alkyl or hydroxyalkyl group is attached to a nitrogen which is a member of a heterocyclic ring, such as a morpholine ring.

Among the preferred tert-amines are the compounds corresponding to the formula RR'R"N in which R is a linear or branched-chain alkyl group containing 6-22 carbons, more preferably a primary alkyl group containing 8-18 carbons; R' is methyl, ethyl, or 2-hydroxyethyl; and R" is independently selected from methyl, ethyl, 2-hydroxyethyl, and linear and branched-chain alkyl groups containing 6-22 carbons. These tert-amines may be used alone or in combination to provide, e.g.:

(1) a single RR'R"N amine in which R is either a linear or a branched-chain alkyl group containing a given number of carbons, (2) a mixture of RR'R"N amines in which the R of one component of the mixture is a linear alkyl group containing a given number of carbons and the R of another component of the mixture is a branched-chain alkyl group containing the same number of carbons, (3) a mixture of RR'R"N amines in which the R of one component of the mixture is a linear alkyl group containing a given number of carbons and the R of another component of the mixture is a linear alkyl group containing a different number of carbons, (4) a mixture of RR'R"N amines in which the R of one component of the mixture is a linear alkyl group containing a given number of carbons, the R of another component is a branched-chain alkyl group containing the same number of carbons, and the R of another component of the mixture is a linear or branched-chain alkyl group containing a different number of carbons, etc.

The most preferred of these tert-amines are those in which at least a majority of alkyl groups in the tert-amine or tert-amine mixture are linear and R' and R" are independently selected from methyl, ethyl, and 2-hydroxyethyl, especially those in which both R' and R" are methyl.

The haloalkanoate which is reacted with the tert-amine to form the betaine is generally a Group IA or IIA metal salt or ammonium salt of an omega-haloalkanoic acid in which the halo substituent is chloro, bromo, or iodo. Neither the size nor the degree of linearity of the alkanoic moiety is critical, but it is most commonly a moiety containing up to about 30 carbons and in which any branching is confined to carbons other than the carbon to which the halo substituent is attached, since any branching on that carbon could be expected to slow the reaction significantly.

Exemplary of the haloalkanoates that can be used are the sodium, potassium, lithium, rubidium, cesium, beryllium, magnesium, calcium, strontium, barium, and ammonium salts of chloroacetic, chloropropionic, chlorobutyric, chloropentanoic, chlorohexanoic, chloroheptanoic, chloro-beta-ethylhexanoic, and corresponding bromo- and iodoalkanoic acids. The preferred haloalkanoates are compounds corresponding to the formula $X(CH_2)_nCOOM$ in which X is chloro, bromo, or iodo; M is alkali metal or ammonium; and n is an integer of 1-6. As in conventional processes, the most preferred haloalkanoate is sodium chloroacetate.

The amount of haloalkanoate employed to quaternize the tert-amine is usually at least the stoichiometric amount.

The polar aprotic solvent utilized in the process may be any such organic solvent in which the betaine is substantially insoluble, at least at room temperature. Such solvents include, e.g., ketones such as 2-propanone, 2-butanone, 3-methyl-2-butanone, 2-pentanone, and 3-pentanone; nitriles such as acetonitrile, propionitrile, butyronitrile, and isobutyronitrile; cyclic ethers such as tetrahydrofuran, tetrahydropyran, and dioxane; sulfoxides such as dimethylsulfoxide; and amides such as hexamethylphosphoramide, N-methylpyrrolidone, dimethylformamide, dimethylacetamide and diethylformamide. However, the preferred solvents are the esters.

Esters which may be used in the process include aliphatic, cycloaliphatic, and aromatic esters, such as the methyl, ethyl, propyl, isopropyl, butyl, isobutyl, t-butyl, pentyl, hexyl, octyl, decyl, dodecyl, cyclohexyl, phenyl, tolyl, and benzyl esters of formic, acetic, propionic, butyric, isobutyric, pentanoic, hexanoic, heptanoic, octanoic, and benzoic acids. The preferred esters are ordinarily the alkyl alkanoates in which both the alkyl and the alkanoic moieties contain about 2-6 carbons, especially ethyl acetate.

The process of the invention is conducted by combining the tert-amine with at least a portion of the haloalkanoate salt in the solvent and allowing the quaternization reaction to occur. It is generally preferred to include all of the haloalkanoate in the initial reaction mixture, but satisfactory results can also be obtained when the salt is gradually added in increments. If desired, some preformed betaine product may also be included in the initial reaction mixture to shorten the time before which any noticeable quaternization occurs.

Although the reaction can be effected at room temperature and atmospheric or subatmospheric pressure, it is ordinarily preferred to use an elevated temperature and/or superatmospheric pressure to speed the reaction. The preferred temperatures are in the range of about 50°–150° C., most conveniently the reflux temperatures of the reaction mixtures; and the preferred pressures are about 0.1–2.1 Mpa. The time required for the reaction depends, of course, on the temperature and pressure used, varying from weeks at room temperature and atmospheric pressure to only minutes at 150° C. and 0.4 Mpa.

The quaternization may be accomplished in a batch process, but a continuous process is apt to be preferred, and any unreacted haloalkanoate remaining in the reaction mixture at the end of the reaction may be recovered and recycled.

Because of the insolubility of the betaine product in the reaction solvent, it is easily recovered as a solid by filtration. The solid thus recovered is a betaine product having high activity; and its activity can be increased to an even higher level, in fact to as high as 100%, by removing some-to-all of the by-product salt and any remaining solvent, if desired.

Actually, it is not necessarily desirable to remove the solvent and by-product salt that remain with the solid betaine after filtration, since the amount of residual solvent is minimal, and the effect that the salt could have in increasing the viscosity of solutions later formed from the betaine could be advantageous in some instances and disadvantageous in others. However, when the objective is to obtain a substantially pure betaine, it is beneficial to separate the betaine and salt by solvent extraction and to supplement the filtration with vacuum drying to remove the remaining solvent.

In a preferred embodiment of the invention, the betaine is recovered by cooling the reaction mixture at the end of the reaction; filtering to separate the betaine and salt from the solvent; washing the salt-contaminated betaine with solvent of the same type used in the reaction, i.e., a non-solvent for the betaine and by-product salt; and then washing with a liquid, such as isopropanol, which is a solvent for the betaine but not the salt.

The following example is given to illustrate the invention and is not intended as a limitation thereof.

EXAMPLE

A suitable reaction vessel was charged with 153 g of N-hexadecyldimethylamine, 54 g of sodium chloroacetate, 15.4 g of preformed betaine derived from the same reactants, and 300 mL of ethyl acetate. The reaction mixture was heated to reflux with stirring and refluxed for eight hours, after which it was cooled and vacuum-filtered to separate the solid betaine/sodium chloride mixture from the solvent and unreacted amine and sodium chloroacetate. A sample of the crude betaine was partially dissolved in refluxing ethyl acetate, gravity-filtered to remove the sodium chloride, and recrystallized to yield 95% active betaine as a tacky, off-white solid.

What is claimed is:

1. In a process for preparing a betaine by reacting a tert-amine with a haloalkanoate salt, the improvement which comprises conducting the reaction in a polar aprotic solvent in which the betaine is substantially insoluble.

2. The process of claim 1 wherein the tert-amine is a compound corresponding to the formula $RR'R''N$ in which R is an alkyl group containing 6–22 carbons; R' is methyl, ethyl, or 2-hydroxyethyl; and R'' is independently selected from methyl, ethyl, 2-hydroxyethyl, and alkyl groups containing 6–22 carbons.

3. The process of claim 2 wherein R is a primary alkyl group containing 8–18 carbons and R' and R'' are independently selected from methyl, ethyl, and 2-hydroxyethyl.

4. The process of claim 3 wherein R' and R'' are methyl.

5. The process of claim 2 wherein R and R'' are independently selected from primary alkyl groups containing 8–18 carbons.

6. The process of claim 5 wherein R' is methyl.

7. The process of claim 1 wherein the haloalkanoate is a compound corresponding to the formula $X(CH_2)_nCOOM$ in which X is chloro, bromo, or iodo; M is alkali metal or ammonium; and n is an integer of 1–6.

8. The process of claim 7 wherein the haloalkanoate is sodium chloroacetate.

9. The process of claim 1 wherein the solvent is an ester, ketone, ether, amide, nitrile, or sulfoxide.

10. The process of claim 9 wherein the solvent is an ester.

11. The process of claim 10 wherein the ester is ethyl acetate.

12. The process of claim 1 which is conducted at a temperature of about 50°–150° C.

13. The process of claim 12 wherein the temperature is the reflux temperature of the reaction mixture.

14. The process of claim 1 which is conducted under superatmospheric pressure.

15. The process of claim 14 which is a batch process.

16. The process of claim 15 wherein a tert-amine corresponding to the formula $RR'R''N$ in which R is a primary alkyl group containing 8–18 carbons and R' and R'' are independently selected from methyl, ethyl, and 2-hydroxyethyl is reacted with sodium chloroacetate in ethyl acetate at reflux temperature.

17. The process of claim 16 wherein R' and R'' are methyl.

18. The process of claim 14 which is a continuous process.

19. The process of claim 18 wherein a tert-amine corresponding to the formula $RR'R''N$ in which R is a primary alkyl group containing 8–18 carbons and R' and R'' are independently selected from methyl, ethyl, and 2-hydroxyethyl is reacted with sodium chloroacetate in ethyl acetate at reflux temperature.

20. The process of claim 19 wherein R' and R'' are methyl.

* * * * *